United States Patent [19]
Kolobow

[11] Patent Number: 5,785,998
[45] Date of Patent: Jul. 28, 1998

[54] APPARATUS FOR MAKING ULTRA THIN WALLED WIRE REINFORCED ENDOTRACHEAL TUBING

[75] Inventor: Theodor Kolobow, Rockville, Md.

[73] Assignee: The United States of America as represented by the Department of Health and Human Services, Washington, D.C.

[21] Appl. No.: 645,886

[22] Filed: May 14, 1996

Related U.S. Application Data

[62] Division of Ser. No. 26,231, Mar. 2, 1993, Pat. No. 5,537,729, which is a continuation of Ser. No. 758,824, Sep. 12, 1991, abandoned.

[51] Int. Cl.$^6$ ............................................. A61M 16/04
[52] U.S. Cl. ..................... 425/110; 118/321; 118/DIG. 4; 425/375
[58] Field of Search .................... 29/460, 469.5, 29/527.1, 527.2, 527.4; 118/321, DIG. 4, DIG. 11; 222/491, 495, 496; 425/100, 101, 110, 269, 272, 363, 375; 427/2, 2.3, 9, 231, 420; 264/215, 309, 310

[56] References Cited

U.S. PATENT DOCUMENTS

| | | |
|---|---|---|
| 3,585,707 | 6/1971 | Stevens . |
| 3,802,908 | 4/1974 | Emmons .................. 117/72 |
| 3,964,488 | 6/1976 | Ring et al. . |
| 4,276,333 | 6/1981 | Cobean .................. 118/321 X |
| 4,440,811 | 4/1984 | Hitaka et al. . |
| 4,687,531 | 8/1987 | Potoczky . |
| 4,956,138 | 9/1990 | Barfield . |
| 4,981,721 | 1/1991 | Krenkel et al. . |
| 5,322,062 | 6/1994 | Serves . |

FOREIGN PATENT DOCUMENTS

| | | |
|---|---|---|
| 0 232 864 | 8/1987 | European Pat. Off. . |
| 232 578 | 8/1987 | European Pat. Off. . |
| 0 383 914 | 8/1990 | European Pat. Off. . |
| 0 490 852 | 6/1992 | European Pat. Off. . |
| 0 515 201 | 11/1992 | European Pat. Off. . |
| 0 559 977 | 9/1993 | European Pat. Off. . |
| 1 160 627 | 7/1958 | France . |
| 3 801 784 | 7/1989 | Germany . |
| 4 535 672 | 11/1970 | Japan . |
| 2 033 759 | 5/1980 | United Kingdom . |
| 93 04725 | 3/1993 | WIPO . |
| 95 01813 | 1/1995 | WIPO . |

OTHER PUBLICATIONS

"A New Thin-Walled Nonkinking Catheter for Peripheral Vascular Cannulation", Kolobow et al. vol. 68, No. 4, pp. 625–629, Oct. 1970, *Surgery*.

*Primary Examiner*—Joseph M. Gorski
*Attorney, Agent, or Firm*—Spencer & Frank

[57] ABSTRACT

An ultra thin walled wire reinforced endotracheal tubing includes a thin walled tubing comprising a polymeric material having a spring material incorporated therewith. Utilization of the spring wire material in combination with polymeric material results in a reduced wall thickness which results in a significant decrease in resistance to air flow through the endotracheal tubing. The endotracheal tubing of the present invention is made by depositing a dissolvable polymeric material on a rotating mandrel in successive layers. A spring material is also applied around the mandrel to produce the ultra thin walled wire reinforced endotracheal tubing. By controlling the rate of deposition of polymeric material along the length of the mandrel, different wall thicknesses of tubing may be achieved.

10 Claims, 4 Drawing Sheets

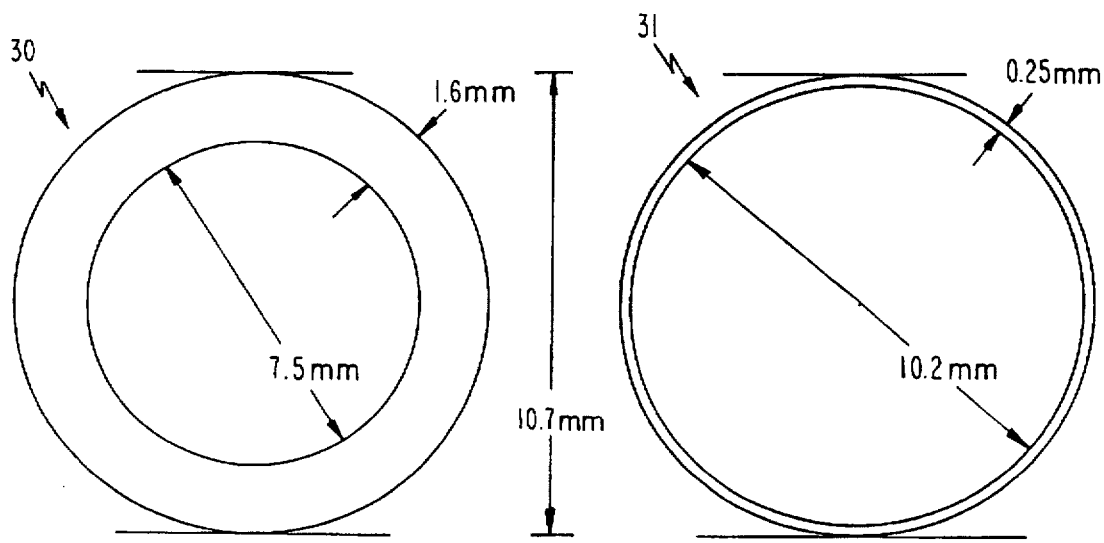
FIG. 2A
PRIOR ART
FIG. 2B
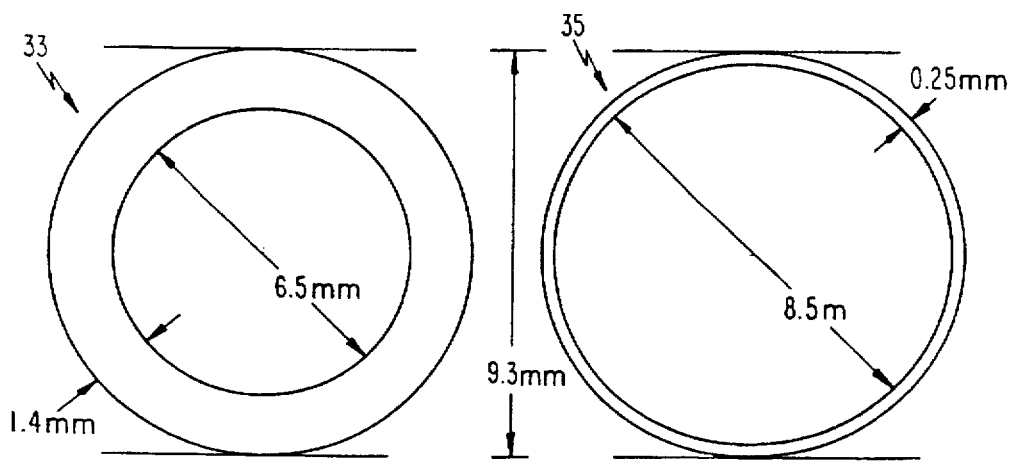
FIG. 3A
PRIOR ART
FIG. 3B

APPARATUS FOR MAKING ULTRA THIN WALLED WIRE REINFORCED ENDOTRACHEAL TUBING

This application is a division of application Ser. No. 08/026,231 filed Mar. 2, 1993 and now U.S. Pat. No. 5,537,729 which is a continuation of Ser. No. 07/758,824 filed Sep. 12, 1991 and now abandoned.

FIELD OF INVENTION

The present invention is directed to an ultra thin walled wire reinforced endotracheal tubing. The ultra thin walled tubing comprises a polymer tube having incorporated therewith a stainless steel spring material. The method of making the tubing comprises coating a rotating Teflon® coated steel mandrel with a polymer material and incorporating a stainless steel spring material therewith. The apparatus includes a polymer supply unit, a pump means to meter the polymer material onto the rotating mandrel and means to dry the polymer as supplied to the mandrel. The ultra thin walled endotracheal tubing reduces airway resistance when compared to standard endotracheal tubes which permits establishment of artificial airways other than mechanical ventilators.

BACKGROUND ART

Endotracheal tubes are widely used in anesthesia and critical care medicine. The endotracheal tube provides access to the upper airways for controlled, assisted ventilation or spontaneous unassisted ventilation with positive end expiratory pressure.

One of the drawbacks of inserting an endotracheal tube into an upper airway of a patient results in the reduction of the lumen of the airway. One manner in which the lumen is reduced is the inability to use the largest possible endotracheal tube for a given patient without subjecting the patient to increased risks. Generally, it is not advisable to insert the largest possible endotracheal tube in the patient since such an attempt will entail many trials and errors which may take additional time, such additional time to be avoided, especially in critical care situations.

In addition, and to maintain endotracheal wall stability, the wall thickness is required having sufficient strength to be safely handled by the using physician or technician. At present, adult endotracheal tubes range between 7 to 9 millimeters in internal diameter, the total wall thickness ranging between 1.4 and 1.5 millimeters. For newborn endotracheal tubes, the decrease in lumen internal diameter as a result of the required wall thickness amounts to approximately 0.5 millimeters or more.

Any decrease in the lumen due to wall thickness has a profound effect on the airway resistance, since the resistance to air flow is inversely proportional to the fourth power of the radius.

As a result of the deficiencies in prior art endotracheal tubes, a need has developed to provide an endotracheal tube having reduced airway resistance so as to facilitate establishment of artificial airways other than those using mechanical ventilators.

Conventional technology used in the fabrication of blood catheters uses either extrusion or dip coating onto mandrels. Extrusion technology has the advantage of low cost, but has little flexibility. With extrusion, the resulting thin wall catheters are rather stiff and are liable to kink or bend to obstruct the inner passageway. The dip coating technique used for currently available catheters and tubes is not reproducible in thin wall gauges and, therefore, wall thickness remain substantial.

In response to this need, the present invention provides an ultra thin walled wire reinforced endotracheal tube which provides reduced airway resistance to permit easier breathing by a patient. The ultra thin walled endotracheal tube comprises a polymer having incorporated therewith a stainless steel spring material to form a continuous tubing. The combination of the polymer and stainless steel spring material provides an ultra thin wall of the tubing which permits the use of an endotracheal tube having similar diameters as prior art tubings but with increased internal diameters and resultant reductions in airway resistance.

SUMMARY OF THE INVENTION

It is accordingly a first object of the present invention to provide an ultra thin walled wire reinforced endotracheal tubing.

It is a further object of the present invention to provide an apparatus for and a method of making ultra thin walled wire reinforced endotracheal tubing.

It is a still further object of the present invention to provide thin walled endotracheal tubing which provides reduced airway resistance when used to establish an artificial airway by having increased inner diameters.

It is a yet further object of the present invention to provide ultra thin walled wire reinforced endotracheal tubing which permits a patient using the tubing to breathe in a more relaxed fashion so as not to become exhausted or tired by attempting to breathe through smaller diameter prior art endotracheal tubes.

In satisfaction of the foregoing objects and advantages, there is provided an ultra thin walled wire reinforced endotracheal tubing which comprises a polymeric material having a stainless spring material incorporated therewith. The combination of the polymeric material and stainless steel spring material permits the endotracheal tube to have an ultra thin wall diameter to provide for an increased air passageway and reduced airway resistance.

An apparatus is provided for making the ultra thin walled wire reinforced endotracheal tubing and includes a coated steel rod, a lathe means for rotating the rod, a liquid polymer supply source, a means for metering the liquid polymer along the length of the steel rod and control means for controlling the thickness of the polymer as applied to the rod to achieve a desired wall diameter. In addition, the stainless steel spring material may be pre-wound and slid over the coated steel rod or, alternatively, means may be provided to coil the spring material around the coated steel rod.

The method of making the ultra thin walled wire reinforced endotracheal tubing generally includes the steps of applying a dissolved polymer to the coated steel rod, incorporating the stainless steel spring material around the polymer coated steel rod, providing an additional amount of polymeric material around the spring material and removing the tubing from the mandrel. Additional embodiments include varying the sequence of applications of polymer material and stainless steel spring material to the rod. The as-applied polymeric material may also be subjected to a drying step using a strip heater with baffles to accelerate the manufacturing process.

BRIEF DESCRIPTION OF DRAWINGS

Reference is now made to the Drawings accompanying the application, wherein:

FIG. 2A shows an end view of a prior art endotracheal tube;

FIG. 2B shows an end view of an endotracheal tube according to the present invention;

FIG. 3A shows an end view of another prior art endotracheal tube;

FIG. 3B shows an end view of a smaller size ultra thin walled wire reinforced endotracheal tube of the present invention;

DESCRIPTION OF THE PREFERRED EMBODIMENTS

The present invention is concerned with endotracheal tubes which provide artificial airways in applications such as anesthesia and critical medicine. The ultra thin walled wire reinforced endotracheal tube of the present invention offers advantages over prior art tubing by providing, for the same outer diameter of tubing, and increased inner diameter and reduced airway resistance. By incorporating a stainless steel spring material with a polymeric material in a thin walled tubing configuration, an endotracheal tube is provided which has sufficient strength to be safely handled by a user.

By providing low air resistance endotracheal tube, whereby patient breathing is made easier, patients may be able to utilize a simpler means of respiratory assistance such as continuous positive airway pressure (CPAP) rather mechanical ventilation means.

In the newborn patient population, the lowering of airway resistance is of vital importance since newborns are more likely to become exhausted or have further difficulty in breathing by using prior art endotracheal tube having significant airway resistance. By utilizing the inventive ultra thin wall wire reinforced endotracheal tubes in newborn patient application, significant reductions in airway resistance are attainable.

In addition, developments and other alternatives for mechanical ventilation such as intratracheal pulmonary ventilation which include a reduction in dead space ventilation and a decrease in airway pressure favor the utilization of establishment of artificial airways having reduced resistance to air flow. As will be described hereinafter, the inventive tubing reduces the wall thickness by 50-80%, thereby resulting in a two- to four-fold decrease in air flow resistance.

Figure 1:
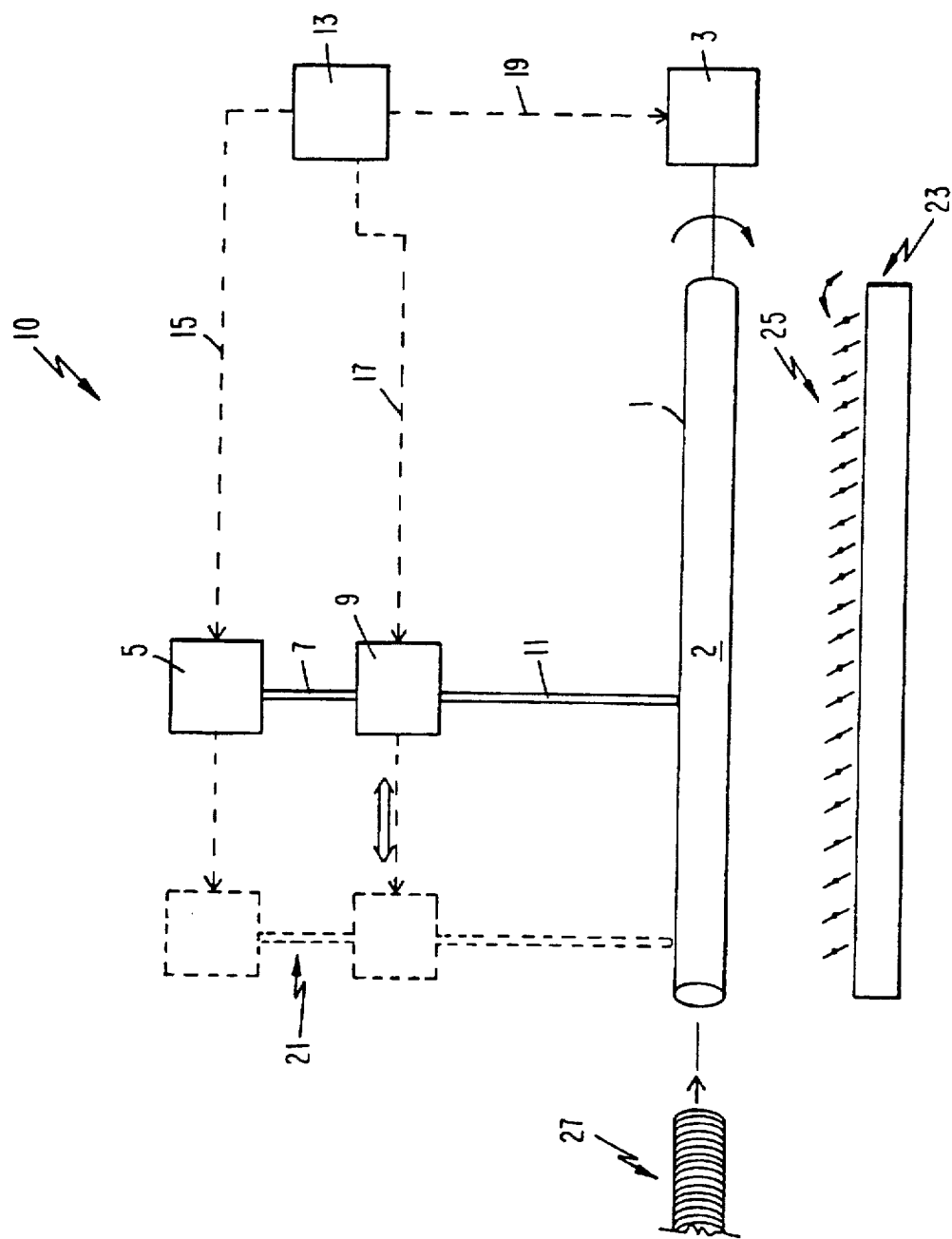
FIG. 1 shows a schematic representation of one embodiment of the apparatus utilized for making the ultra thin walled wire reinforced endotracheal tubing.

With reference now to FIG. 1, a schematic representation of an apparatus adapted for making ultra thin walled wire reinforced endotracheal tube is illustrated. The apparatus is generally designated by the reference numeral 10 and is seen to include a cylindrical mandrel 1 having a release agent coating on the surface 2 thereof. The release agent 2 is designed to facilitate removal of the ultra thin walled wire reinforced endotracheal tubing from the cylindrical mandrel 1. The release agent may be any agent known in the art such as Teflon®. The cylindrical mandrel may be made of any material having sufficient strength to provide support for the tubing, preferably a steel rod.

The cylindrical mandrel is connected to a lathe means 3 which includes drive means therewith to rotate the mandrel at a predetermined speed. Of course, any known means capable of rotating a cylindrical mandrel may be utilized in substitution for the lathe 3.

The apparatus for making the ultra thin walled wire reinforce endotracheal tubing also includes a polymer source means 5 which supplies a dissolvable polymer such as polyurethane Lycra® under pressure to a metering pump 9 via the line 7. The polymer source means may be a closed container including a source of inert gas to provide the pressure to supply the dissolved polymer to the metering pumping 9. Preferably, the source of the pressure is a dry nitrogen or other inert gas.

The metering pump 9 includes a nozzle 11 made out of a flexible tubing such as Teflon®. The tubing 11 should have sufficient flexibility and thickness to follow the contours of the cylindrical mandrel 1 and float on the polymer layer as it emerges from the nozzle. The flexibility of the tubing 1 may be enhanced by the addition of a spring material surrounding the tubing. The metering pump 9 may be a gear fluid pump designed to meter a solution of polymer onto the mandrel.

The polymer source means 5 and metering pump means 9 also include a cross feed means which permits the source means 5, metering means 9 and nozzle 11 to traverse the length of the mandrel 1. As illustrated by the reference numeral 21 in FIG. 1, the source means 5, metering pump 9 and nozzle 11 are displaced along the longitudinal axis of the cylindrical mandrel 1. The longitudinal movement of the nozzle 11 permits that polymer to be continuous applied to the mandrel over a preselected pattern.

A control means 13 is provided that regulates the deposition of the polymer on the mandrel 1. The control means is connected to the polymer source means 5 via the line 15, the metering pump 9 via the line 17 and the lathe 3 via the line 19. By controlling the rotation of the mandrel 1 via the lathe 3 and the amount of polymer deposited on the mandrel 1, the thickness of polymer applied to the mandrel or wall thickness of the ultra thin walled and wire reinforced endotracheal tubing may be controlled and varied. The control means 13 also provides control over longitudinal traversing of the nozzle 11 and associated components and the cylindrical mandrel 1. It should be understood that, although the nozzle 11, metering pump 9 and polymer source means 5 are depicted as longitudinally traversing the length of the cylindrical mandrel 1, in another embodiment, the polymer source means 5 may be stationery with the metering pump 9 and nozzle 11 traversing the length of the mandrel 1. It should be understood that the mechanism for providing the longitudinal traversing movement of either the metering pump 9 and nozzle 11 or these components with the polymer source means 5 are well recognized in the prior art. For example, these components may be longitudinally traversed using a drive means and rack and pinion gearing.

The apparatus 10 also includes a heating means 23 which supplies heat such as hot air to the mandrel 1 to dry the polymer solution after deposition on the mandrel.

The heating means may a strip heater or other known heating means. The heating means 23 may also include individually adjustable baffles 25 which facilitate directing the hot air toward the mandrel 1. The adjustable feature of the baffles 25 permit varying the amount of drying air along the length of the mandrel 1. For example, when producing a tapered endotracheal tube, certain areas of the tube having increased wall thickness require a higher heat input for drying purposes. In this situation, the individually adjustable baffles are arranged to direct more hot air to the portion of the cylindrical mandrel having the endotracheal tube with increased wall thickness.

FIG. 1 also depicts a coil spring 27 which is designed to be inserted over the Teflon® coated cylindrical mandrel 1. The spring 27 may be manually inserted over the rod or, alternatively, by known mechanical means. As an alternative embodiment, the spring material may be in the form of an unwound wire or flat material and be wound around the cylindrical mandrel in a known fashion. As will be described hereinafter, the spring 27 may be applied to the mandrel 1 after or during the deposition of the polymeric material.

The method of making the ultra thin walled wire reinforced endotracheal tubing will now be described. In the first embodiment, a polymeric material such as a polyurethane Lycra® is dissolved in a compatible solvent. A typical concentration of polymeric material would range between 25-28 weight percent polymer in the solvent. This range is only exemplary and more or less concentrations of polymeric material may be utilized depending on the particular polymer being employed. The dissolved polymer is supplied to a metering pump under pressure such as dry nitrogen. The metering pump, such as a fluid gear pump, meters the dissolved polymer unto the rotating surface of the mandrel while the nozzle traverses the length of the cylindrical mandrel. The deposited polymer is permitted to air dry, or alternatively, dry by application of a source of heat such as a strip heater or the like. This sequence may be repeated if an increased thickness of polymeric material is desired on the surface of the cylindrical mandrel.

By choosing a particular rate of deposition of polymeric material, the solvent evaporation rate can be optimized such that one layer of polymer can be deposited onto the previously deposited and dried layer to build up thickness. In a further embodiment, successive deposition of several layers of polymeric solution may be performed while traversing the cylindrical mandrel on a single run. In this embodiment, a plurality of nozzles may be utilized which are spaced apart from each other such that following nozzles are depositing polymeric material to an already dried polymeric material layer.

Once the initial layer or layers of polymeric solution are deposited on the cylindrical mandrel a spring material, preferably a stainless steel spring, is applied to the cylindrical mandrel. In one embodiment, the stainless steel spring may be in an uncoiled configuration, either flat or round in size, and wound around the polymer-coated mandrel by known mechanical means. Alternatively, the stainless steel spring may be provided in a pre-coiled configuration and inserted over the mandrel.

The choice of winding per inch for the spring or the diameter or cross-sectional area of the spring material may vary depending upon the desired spring properties and flexibility of the ultra thin walled wire reinforced endotracheal tube. Furthermore, it should be understood that the spring material cross-sectional area, or diameter if the spring material is round, is sized to provide the ultra thin walled wire reinforced endotracheal tubing having a reduced wall thickness while maintaining sufficient strength to avoid kinking or bending during handling and subsequent constriction of an airway passage.

Once the spring wire is applied to the mandrel, further deposition of polymeric material may be performed to yield a smooth outside surface having the desired final diameter.

In a further embodiment, the spring material may be wound around the mandrel or inserted thereover, simultaneously with the application of the polymer solution.

With reference to FIGS. 2A and 2B, a comparison is illustrated between prior art endotracheal tubes and the ultra thin walled wire reinforced endotracheal tubing of the present invention. As can be seen from FIG. 2A, the prior art endotracheal tube having an outer diameter of 10.7 millimeters has an inner diameter of 7.5 millimeters due to the wall thickness of 1.6 millimeters. In contrast, the ultra thin wall wire reinforced endotracheal tubing of the present invention may be made having the same outer diameter of 10.7 millimeters but with an increased inner diameter of 10.2 millimeters as a result of the reduced wall thickness of 0.25 millimeters.

Referring to FIGS. 3A and 3B, a similar comparison is made wherein the prior art endotracheal tubing 33 is compared to the ultra thin walled wire reinforced endotracheal tubing 35 of the present invention. In this manner, the prior art endotracheal tubing 33 having an outer diameter of 9.3 millimeters has an inner diameter of 6.5 millimeters. The ultra thin walled wire reinforced endotracheal tubing 35 has an increase in the inner diameter to 8.8 millimeters for the same 9.3 millimeter outside diameter.

Figure 4:
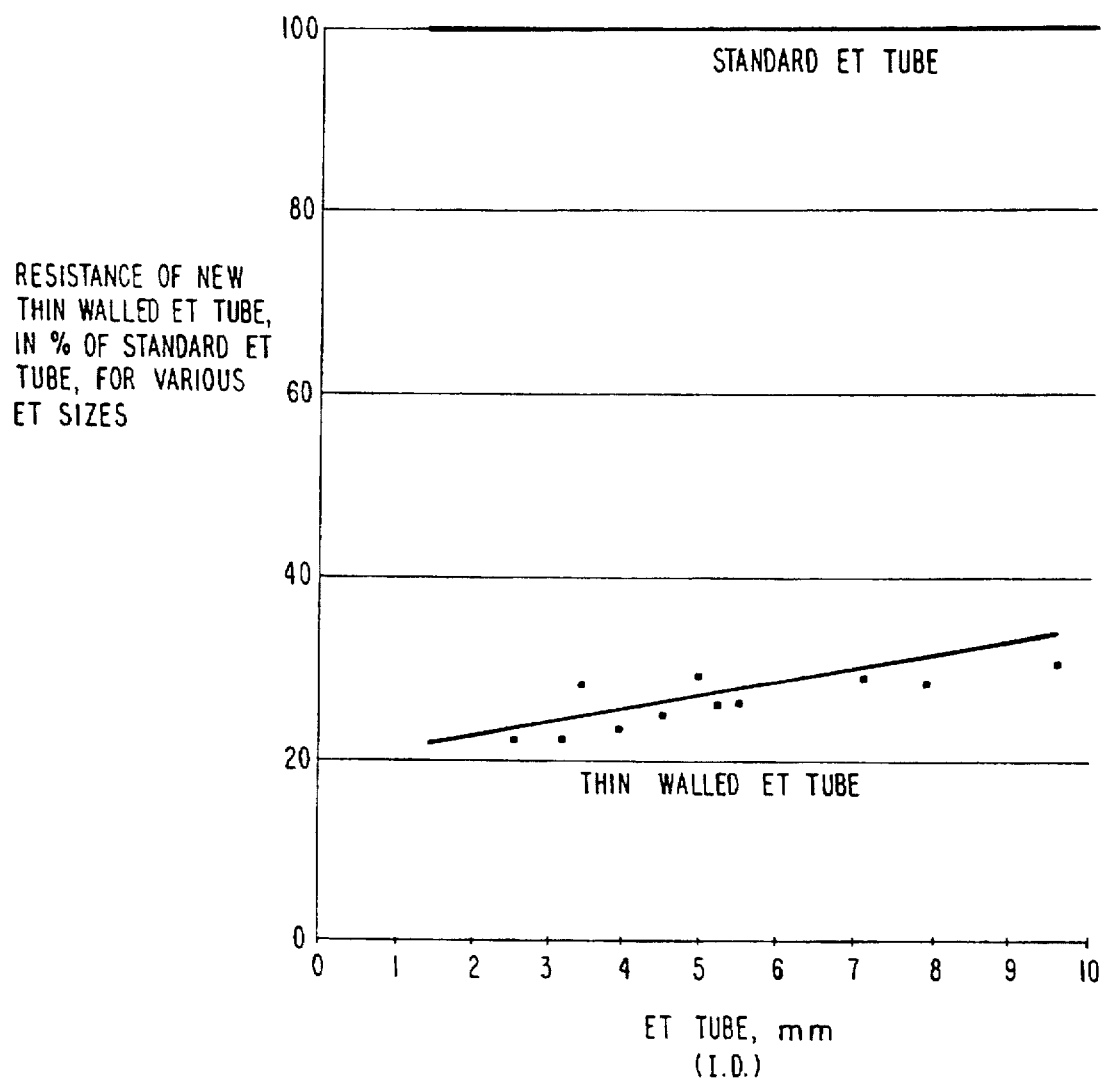
FIG. 4 shows a graph comparing air resistance in the inventive ultra thin walled endotracheal tube as compared to prior art endotracheal tubes.

With reference now to FIG. 4, a graph is depicted which compares standard endotracheal tubes such as those depicted in FIG. 2A and 3A with the ultra thin walled wire reinforced tubing of the present invention having a wall thickness of approximately 0.25 millimeters. The graph compares the resistance of the inventive thin walled endotracheal tubing as a percent of the air resistance of the standard endotracheal tubing for a range of endotracheal tubing based upon inner diameters. As can be seen from the graph in FIG. 4, the inventive thin walled endotracheal tubing results in a substantial decrease in resistance as compared to prior art endotracheal tubing. In addition, air flow resistance is further lowered for smaller sized endotracheal tubes which provides reduced air resistance in endotracheal tubing adapted for newborn patients.

Figure 5:
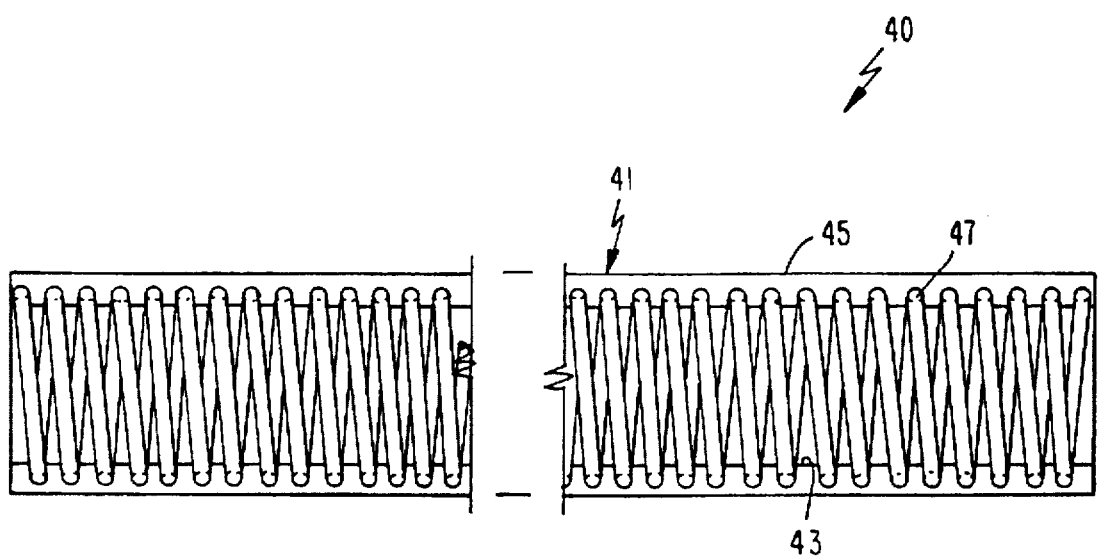
FIG. 5 shows an exemplary ultra thin walled wire reinforced endotracheal tube showing the spring material incorporated in the endotracheal tubing wall.

With reference now to FIG. 5, an exemplary ultra thin walled wire reinforced endotracheal tubing is generally designated by the reference numeral 40. The thin walled wire reinforced endotracheal tubing includes a tubing wall 41 having an inner surface 43 and outer surface 45. Incorporated within the tubing wall 41 is a spring 47. The diameter of the spring material 47 is sized in conjunction with the applied layers of polymeric material to provide the minimum wall thickness while maintaining sufficient strength to permit handling of the endotracheal tube. As disclosed above, a wall thickness of about 0.25 millimeters is attainable using the inventive method and apparatus for making the ultra thin walled wire reinforced endotracheal tubing. The wall thickness of about 0.25 mm is a preferred thickness with the wall thickness ranging between about 0.1 mm and 0.5 mm. A preferred range for the wall thickness includes between about 0.15 mm and 0.35 mm. For a given wall thickness of 0.25 millimeters, it should be understood that the diameter of the wire spring material is less than the wall thickness to provide a polymeric layer along the inner and outer surfaces, 43 and 45 respectively of the tube 40. Alternatively, the wire spring material when positioned on the cylindrical mandrel prior to deposition of polymeric material may form part of the inner surface 43 of the tubing 40.

The apparatus and method of making the ultra thin walled wire reinforced endotracheal tubing provides a endotracheal tube having a thin wall thickness not attainable in prior art endotracheal tube making apparatus or method. The inventive apparatus and method also provide flexibility in adapting the manufacture of the inventive endotracheal tubing for various configurations for operating conditions such as an eccentric or slightly out of round mandrel. By having the nozzle of the metering pump 9 float or follow the contour of the mandrel, any slight out of roundness and/or eccentricity of the mandrel can be easily accommodated without effecting the quality of the tube.

In addition, the method of applying the polymer solution along the length of the mandrel permits programming of the control means to achieve different tubing configuration. For example, by increasing the flow rate of the dissolved polymer or reducing the rotation of the mandrel in conjunction with controlling the travel of the nozzle 11 along the mandrel, varying thicknesses of wall tubing may be obtained. By programming of more layers of different thicknesses on different parts of the mandrel, utilizing the control means, tapered endotracheal tubes may be manufactured. Alternatively, the mandrel 1 may be made having a tapered configuration wherein a tapered spring material may be used in conjunction with a uniform coating to produce a tapered tube having a uniform wall thickness.

As such, an invention has been disclosed in terms of preferred embodiments which fulfill each and every one of the objects of the present invention as set forth hereinabove and provides a new and improved ultra thin walled wire reinforced endotracheal tubing as well as an apparatus and method for manufacturing thereof.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. An apparatus for making an ultra thin walled wire reinforced endotracheal tubing comprising:
   a) a polymer solution source means;
   b) a mandrel;
   c) means to rotate said mandrel;
   d) a metering pump means further comprising a nozzle for depositing said polymer solution onto said mandrel;
   e) means to longitudinally traverse at least said nozzle along the length of said mandrel; and
   f) said nozzle being of flexible material such that as the polymer solution emerges therefrom and is forced onto the mandrel, the polymer solution forces the nozzle away from the mandrel and causes the nozzle to float thereon, whereby the nozzle follows a contour of the mandrel and the polymer solution is forced around a spring wire applied around the mandrel such that the spring wire becomes incorporated within the polymer solution.

2. The apparatus of claim 1 further comprising heating means for solidifying said polymer solution on said mandrel.

3. The apparatus of claim 2 wherein said heating means further comprises a strip heater for flowing hot air across said mandrel.

4. The apparatus of claim 3 further comprising baffle means for adjusting flow of said hot air along the length of said mandrel.

5. The apparatus of claim 1 further comprising control means for regulating deposition of said polymer solution, speed of rotation of said mandrel and longitudinal traversing of at least said nozzle to vary the thickness of polymer solution deposited on said mandrel.

6. The apparatus of claim 1 wherein said metering pump means further comprises a fluid gear pump.

7. An apparatus for making an ultra thin walled wire reinforced endotracheal tubing comprising:
   a) a polymer solution source means;
   b) a mandrel;
   c) means to rotate said mandrel;
   d) a metering pump means further comprising a nozzle for depositing said polymer solution onto said mandrel;
   e) means to longitudinally traverse at least said nozzle along the length of said mandrel;
   f) heating means for solidifying said polymer solution on said mandrel;
   g) control means for regulating deposition of said polymer solution, speed of rotation of said mandrel and longitudinal traversing of at least said nozzle to vary the thickness of polymer solution deposition on said mandrel; and
   h) said nozzle being of flexible material such that, as the polymer solution emerges therefrom and is forced onto the mandrel, the polymer solution forces the nozzle away from the mandrel and causes the nozzle to float thereon, whereby the nozzle follows a contour of the mandrel and the polymer solution is forced around a spring wire applied around the mandrel such that the spring wire becomes incorporated within the polymer solution.

8. The apparatus of claim 7 wherein said metering pump means further comprises a fluid gear pump.

9. The apparatus of claim 8 wherein said heating means further comprises a strip heater for flowing hot air across said mandrel.

10. The apparatus of claim 9 further comprising baffle means for adjusting flow of said hot air along the length of said mandrel.

* * * * *